United States Patent [19]

Hirano et al.

[11] Patent Number: 4,503,071

[45] Date of Patent: Mar. 5, 1985

[54] INSECTICIDAL COMPOSITION CONTAINING OPTICALLY ACTIVE α-CYANO-3-PHENOXYBENZYL 2-(4-CHLOROPHENYL)ISOVALERATE

[75] Inventors: Masachika Hirano, Osaka; Isao Ohno, Hyogo; Nobuo Ohno, Osaka; Akihiko Mine, Osaka, all of Japan

[73] Assignee: Sumitomo Chemical Company, Limited, Osaka, Japan

[21] Appl. No.: 825,507

[22] Filed: Aug. 17, 1977

[30] Foreign Application Priority Data

Aug. 18, 1976 [JP] Japan .................................. 51-99071

[51] Int. Cl.³ ...................... A01N 53/00; C07C 69/743
[52] U.S. Cl. ................................. 514/521; 260/465 D
[58] Field of Search .................... 424/304; 260/465 D

[56] References Cited

U.S. PATENT DOCUMENTS 3,996,244 12/1976 Fujimoto et al. .................. 424/282
4,000,181 12/1976 Elliott et al. .................... 260/465 D

*Primary Examiner*—Nicky Chan
*Attorney, Agent, or Firm*—Sughrue, Mion, Zinn, Macpeak and Seas

[57] ABSTRACT

An insecticidal composition comprising, as an active ingredient, an optically active α-cyano-3-phenoxybenzyl 2-(4-chlorophenyl)isovalerate and an inert carrier having a strong insecticidal activity without any appreciable toxicity to plants as well as to mammals.

13 Claims, No Drawings

INSECTICIDAL COMPOSITION CONTAINING OPTICALLY ACTIVE α-CYANO-3-PHENOXYBENZYL 2-(4-CHLOROPHENYL)ISOVALERATE

BACKGROUND OF THE INVENTION

1. Field of the Invention

This invention relates to an insecticidal composition comprising, as an active ingredient, an optically active isomer of α-cyano-3-phenoxybenzyl 2-(4-chlorophenyl)isovalerate (of the acid moiety or both the acid and alcohol moieties of the compound) represented by the formula (I)

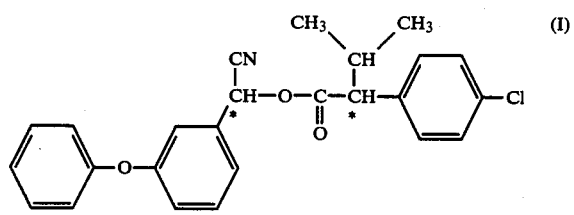

which exhibits a remarkable insecticidal activity without any appreciable toxicity to plants as well as to mammals.

The insecticidal composition according to the present invention is very useful since it can be used in farms and gardens for sanitary use, in grain stores and in forestry.

2. Description of the Prior Art

At present, an extract of pyrethrum flowers (containing pyrethrin) and allethrin which is a synthetic analog of the active component of the extract of pyrethrum flowers are generally used as rapid active insecticides having no appreciable toxicity to human or animals. However, in spite of their excellent utility, the use of pyrethrum flower extract is limited due to its relatively high production cost. Moreover, these compounds are unstable to light and, thus, they tend to rapidly lose their activity in the field when used in gardens.

As a result of synthesizing various compounds and optically active isomers thereof and testing their biological activities, it was found that the optically active isomers of the compound represented by formula (I) above showed excellent insecticidal activities in respect to insects such as flies and mosquitoes which are harmful to hygiene and agriculturally injurious insects such as plant-hoppers, leaf hoppers, aphids, boll worms, diamondback moths and army worms, while having no phytotoxicity on crops and plants and low toxicity to human and animals. It was also found that these isomers can be produced comparatively cheaply.

It is well known that the racemate α-cyano-3-phenoxybenzyl 2-(4-chlorophenyl)isovalerate has an insecticidal activity as disclosed in U.S. Pat. No. 3,996,244. However, when the present inventors synthesized the optically active isomers on the acid and alcohol moieties of this compound and supplied them for biological assay, they discovered that the ester of the S(+) acid had a stronger insecticidal activity than the racemate. In particular, even stronger activity was shown by the ester of the S(+) acid and the S(−) alcohol. Moreover, in the case of many crops and plants, racemic α-cyano-3-phenoxybenzyl 2-(4-chlorophenyl)isovalerate exhibits a phytotoxicity causing partial chlorosis of the new shoots. However, with the ester of the S(+) acid and racemic alcohol and the ester of the S(+) acid and the S(−) alcohol discovered by the present inventors, the chlorosis was found to be low enough to cause no phytotoxicity at practical concentrations. Thus, the inventors found that these isomers are extremely beneficial as insecticides. The fact that the optically active isomers consisting of this specific combination of the acid moiety and the alcohol moiety simultaneously have extremely strong insecticide activity and no practical phytotoxicity to crops and plants is novel and a completely unexpected finding.

DETAILED DESCRIPTION OF THE INVENTION

The optically active compounds of this invention include the following compounds:

Compound (1)

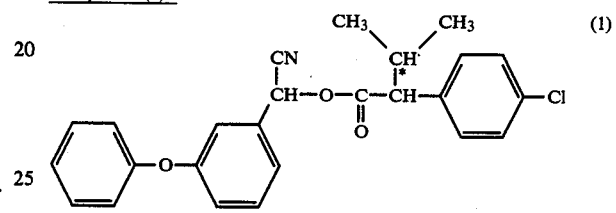

The ester of the S(+) acid and the racemic alcohol.

Compound (2)

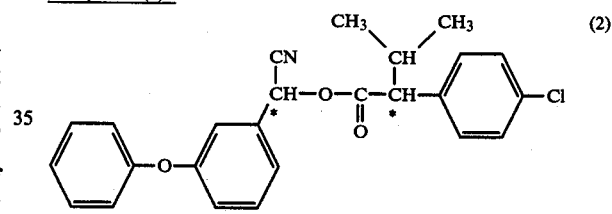

The ester of the S(+) acid and the S(−) alcohol. The asterisks in the general formulas indicate the asymmetric carbon atoms.

The insecticidally active compound of this invention can be prepared by a conventional procedure as disclosed in U.S. Pat. No. 3,966,244. Typically, the compound can be prepared by esterification of an optically active acid, i.e., S-(+)-2-(4-chlorophenyl)isovaleric acid, and an alcohol, i.e., 3-phenoxymandelonitrile in a appropriate inert solvent. The optically active acid can be obtained, for example, by the procedure set forth in Japanese Patent Application (OPI) No. 25544/75. The above esterification can be advantageously carried out using an acid halide, preferably an acid chloride, i.e., 2-(4-chlorophenyl)isovaleroyl chloride, at room temperature or below in the presence of an acid acceptor, for example, an organic tertiary amine such as pyridine, triethylamine and the like. In the esterification, the presence of an inert solvent is not essential, but it is generally preferred to use a solvent in order to assure a smooth reaction. Any solvent which is inert to the reactants and the ester product may be used and preferred inert solvents include benzene, toluene and petroleum benzine.

Alternatively, the insecticidally active compound of this invention can be prepared by reacting a halide or sulfoxylate of the above alcohol, i.e., an α-halo-3-phenoxyphenylacetonitrile, with an alkali metal salt, a silver salt or an organic tertiary base salt of S-(+)-2-(4-chlorophenyl)isovaleric acid. These salts may be formed in situ by adding simultaneously the acid and the corresponding base to the reaction system. In this case, a solvent such as benzene, toluene, acetone, dimethylformamide and the like is preferably used, and the reaction is preferably conducted by heating the reaction system at or below the boiling point of the solvent used. Preferred halogens for the halide of alcohol are chlorine and bromine. Further, the insecticidally active compound of this invention can be prepared in the manner as described in, for example, British Pat. No. 1,122,658 (M. F. Soulal and M. C. Woodford) and *Chemical Abstracts*, 70 3831c (1969). That is, 3-phenoxybenzaldehyde, sodium cyanide and S-(+)-2-(4-chlorophenyl)isovaleroyl chloride are mixed simultaneously while stirring thereby allowing them to react with each other. The reaction temperature and the reaction time varies depending upon the type of the solvent used, but the reaction can be carried out at a temperature in the range of from about 0° to about 150° C., preferably 10° to 100° C. for about 5 to about 24 hours. Any inert solvent may be used in the reaction; pentane, hexane, heptane, higher alkanes, benzene, toluene, xylene and the like are preferred.

The reaction product obtained in the above reaction is generally a mixture of S-(−)-α-cyano-3-phenoxybenzyl S-(+)-2-(4-chlorophenyl)isovalerate and R-(+)-α-cyano-3-phenoxybenzyl S-(+)- 2-(4-chlorophenyl)isovalerate due to the presence of an additional asymmetric center in the alcohol reactant. This mixture can be optically resolved in a conventional manner, for example, a procedure described by E. L. Eliel, *Stereochemistry of Carbon Compounds*, P 49 (1962), published by McGraw-Hill Book Company (N.Y.).

The method of synthesis and insecticidal activity of the compounds of this invention will now be explained in detail with reference to the following Reference Example and Examples. Unless otherwise indicated, all parts, ratios and the like are by weight.

REFERENCE EXAMPLE 1

1.36 g of pyridine and 1.94 g of 3-phenoxymandelonitrile were dissolved in 30 ml of anhydrous benzene. While cooling to below 5° C. in an ice-water bath, a solution formed by diluting 2.0 g of S-(+)-2-(4-chlorophenyl)isovaleroyl chloride ($[\alpha]_D^{20}$ +51.5° (neat)) in 10 ml of anhydrous benzene was added dropwise. After completion of the addition, the ice-water bath was removed, and the mixture was stirred for 3 hours at room temperature. The aqueous layer was extracted twice with 10 ml of benzene, and the extract was combined with the organic layer obtained above. The combined organic layer was washed successively with 10 ml of 10% hydrochloric acid, a saturated aqueous solution of sodium bicarbonate and a saturated aqueous solution of sodium chloride, and then dried over anhydrous sodium sulfate. The solvent was removed by distillation under reduced pressure to obtain the desired α-cyano-3-phenoxybenzyl S-(+)-2-(4-chlorophenyl)isovalerate (1) (yield 3.50 g; $n_D^{18.5}$ 1.5684; $[\alpha]_D^{21}$ −9.53° (CHCl$_3$)).

REFERENCE EXAMPLE 2

9.88 g of S-(+)-2-(4-chlorophenyl)isovaleric acid ($[\alpha]_D^{20}$ +48.3° (CHCl$_3$)) was added to 5.81 g of an aqueous solution of 30% sodium hydroxide to form a sodium salt of the acid. To the mixture was added 0.34 g of tetrabutyl ammonium bromide dissolved in 19.3 g of water. Then, 18.7 g of toluene was added to the mixture and the resulting mixture was stirred until the temperature reached 70° C. A solution obtained by dissolving 11.96 g of α-bromo-3-phenoxyphenylacetonitrile in 17.9 g of toluene, maintained at the same temperature as above, was added dropwise to the above mixture over a period of 1 hour. After completion of the addition, the temperature was increased to 75° C. and was maintained at this level for 4 hours while stirring. After cooling to room temperature, the layers were separated, and the organic layer was washed twice with 10 ml of a 5% aqueous sodium carbonate solution, and then washed 3 times with 10 ml of water. The solvent was removed by distillation under reduced pressure to obtain the desired ester α-cynano-3-phenoxy-benzyl S-(+)-2-(4-chlorophenyl)isovalerate (yield 17.3 g; $n_D^{22.0}$ 1.5680; $[\alpha]_D^{22}$ −9.60° (CHCl$_3$)).

REFERENCE EXAMPLE 3

To a solution in 40 ml of n-heptane of 9.91 g of 3-phenoxy-benzaldehyde and 11.57 g of S-(+)-2-(4-chlorophenyl)isovaleroyl chloride ($[\alpha]_D^{20}$ +51.49° (neat)) was added dropwise an aqueous solution containing 3.09 g of 95% sodium cyanide and 0.10 g of benzyltriethylammonium chloride dissolved in 30 ml of water while keeping at room temperature in a water bath. Stirring was continued for 8 hours at an internal temperature of 25° to 30° C., and the layers were separated at an internal temperature of over 50° C. in order to attain the layer separation effectively. The n-heptane layer was washed twice with water, and the solvent was then removed by distillation under reduced pressure to obtain the desired ester α-cyano-3-phenoxybenzyl S-(+)-2-(4-chlorophenyl)isovalerate (yield 21.08 g; $n_D^{22.0}$ 1.5682; $[\alpha]_D^{22.0}$ −11.9° (CHCl$_3$)).

REFERENCE EXAMPLE 4

5 g of the α-cyano-3-phenoxybenzyl S-(+)-2-(4-chlorophenyl)isovalerate obtained in Reference Example 2 was adsorbed on a column packed with 150 g of silica gel and the column was eluted with a mixed solvent consisting of n-hexane and ethyl acetate (40:1 by volume). The isomeric ratio of each fraction was determined by gas-chromatographic analysis under the conditions given below and the fractions consisting of the isomer which was eluted later on the gas chromatography were collected and concentrated to obtain 0.5 g of the desired S-(−)-60 -cyano-3-phenoxybenzyl S-(+)-2-(4-chlorophenyl)isovalerate ($n_D^{22}$ 1.5673; $[\alpha]_D^{22}$ −11.18° (CHCl$_3$)). Conditions for Gas Chromatographic Analysis of Isomer Column: 2% Silicone Gum DC-QF-1

Carrier: Chromosorb W-AW-DMCS
Length: 1.2 m
Column Temperature: 220° C.
Temperature of Vaporization Chamber: 250° C.
Carrier Gas: Nitrogen 40–45 ml/min.

(The retention periods of each isomer under the same conditions were 7 minutes and 8 minutes, with the (−, +) isomer having the longer retention period.

EXAMPLE 1

Insecticidal Efficacy against *Spodoptera litura*

20% emulsifiable concentrates were prepared by the method set forth in Preparation Example 2 hereof using Compounds (1) and (2) of this invention and the racemate. A 20% emulsifiable concentrate of dimethyldichlorovinyl phosphate (DDVP) was also prepared as a standard.

Samples of the above emulsifiable concentrates diluted with water as a diluent (10 ml in each case) were sprayed onto Chinese cabbage grown in pots of the 3-4 leaf stage, the leaves dried in a stream of air and then cut off to be placed in a high-waisted glass chalet of diameter 14 cm, height 7 cm. Ten 3rd instar larvae of *Spodoptera litura* were released inside, and the number which were alive and dead after 2 days was noted to evaluate the $LC_{50}$ (50% lethal concentration) value. The results obtained are shown in Table 1 below.

TABLE 1

| Test Compound | $LC_{50}$ (ppm) | Relative Efficacy* |
|---|---|---|
| (1) | 5.0 | 240 |
| (2) | 1.7 | 587 |
| Racemate | 12 | 100 |
| DDVP | 450 | 2.7 |

*Racemate taken as 100.

EXAMPLE 2

Insecticidal Efficacy against *Musca domestica*

Compounds (1) and (2) of this invention and the racemate were each diluted to the desired concentration with acetone and 0.5 μl was dropped onto the thoracic dorsal plate of *Musca domestica* of the CSMA strain (a sensitive strain fixed by the Chemical Specialities and Manufactures Associations) with a microsyringe. The treated insects were introduced into a plastic cup of diameter 11 cm into which food (3% sugar water) had been inserted. After 24 hours, the number of alive and dead was noted to evaluate $LD_{50}$ value. The results obtained are shown in Table 2 below.

TABLE 2

| Test Compound | $LD_{50}$ (μg/fly) | Relative Efficacy* |
|---|---|---|
| (1) | 0.014 | 221 |
| (2) | 0.0055 | 564 |
| Racemate | 0.031 | 100 |

*Racemate taken as 100.

EXAMPLE 3

Insecticidal Efficacy against *Culex pipiens pallens* Larvae 20 percent emulsifiable concentrates as indicated in Preparation Example 2 hereof of Compounds (1) and (2) of the present invention and the racemate were diluted to the desired concentration and introduced into a 300 ml glass beaker, together with a group of 30 last instar larvae of *Culex pipiens pallens*. The number of alive and dead after 24 hours was noted to evaluate the $LC_{50}$ value found from the mortality. The results obtained are shown in Table 3 below.

TABLE 3

| Test Compound | $LC_{50}$ | Relative Efficacy* |
|---|---|---|
| (1) | 0.018 | 244 |
| (2) | 0.010 | 440 |
| Racemate | 0.044 | 100 |

*Racemate taken as 100.

EXAMPLE 4

Phytotoxicity to Vegetables

Seeds of the following vegetables were sown in a 10 cm plant pot and grown until the stage of 1-2 main leaves. Emulsifiable concentrates were prepared by the method set forth in Preparation Example 2 hereof using Compounds (1) and (2) of this invention and the racemate diluted to the required concentration with water and sprayed on the seedlings of each vegetable. The phytotoxicity 1 week after the spraying was noted. The test vegetables used in the tests were as follows.

| Name of Vegetable | Variety | Stage at which Spraying Carried out |
|---|---|---|
| Chinese Cabbage (*Brassica spp.*) | "Muso" | 1.5-2 leaf stage |
| Japanese Radish (*Raphanus sativus*) | "Mino Wase" | 2-2.5 |
| Tomato (*Lycopersicon esculentum*) | "Sekai Ichi" | 2 |
| Cucumber (*Cucumis sativus*) | "Kaga Aonaga" | 1.5 |
| Egg-plant (*Solanum melongena*) | "Makuro" | 2 |

The results obtained are shown in Table 4 below.

TABLE 4

| Test Compound | Conc. (ppm) | Degree of Phytotoxicity* | | | | |
|---|---|---|---|---|---|---|
| | | Chinese Cabbage | Japanese Radish | Tomato | Cucumber | Egg-plant |
| (1) | 800 | 1.7 | 1.5 | 1.0 | 1.8 | 1.6 |
| | 400 | 1.4 | 1.0 | 0.6 | 0.8 | 0.4 |
| | 200 | 0.8 | 0.1 | 0 | 0.2 | 0 |
| | 100 | 0 | 0 | 0 | 0 | 0 |
| | 50 | 0 | 0 | 0 | 0 | 0 |
| (2) | 800 | 0 | 0.2 | 0.1 | 0 | 0 |
| | 400 | 0 | 0 | 0 | 0 | 0 |
| | 200 | 0 | 0 | 0 | 0 | 0 |
| | 100 | 0 | 0 | 0 | 0 | 0 |
| | 50 | 0 | 0 | 0 | 0 | 0 |
| Racemate | 800 | 3.8 | 4.0 | 2.3 | 3.0 | 2.6 |
| | 400 | 2.5 | 2.8 | 1.0 | 2.5 | 1.8 |
| | 200 | 2.3 | 2.2 | 1.0 | 2.1 | 1.5 |
| | 100 | 1.3 | 1.5 | 0.5 | 1.2 | 0.2 |
| | 50 | 0.9 | 0.2 | 0.4 | 1.0 | 0 |

*Estimates were made from 0 (normal)-5 (total chlorosis), and average values were calculated.

The concentration of the compounds of this invention which is actually used in fields by spray is about 100 ppm. It is clear that, in comparison with the racemate, Compound (2) of this invention has unexpectedly excellent characteristics in that it can be used from 100 to 400 ppm without any phytotoxicity at all; Compound (1) is also superior in that it has no phytotoxicity at 100 ppm whereas at 100 ppm the racemate has a phytotoxicity effect on many vegetables.

EXAMPLE 5

Field Trials

20% emulsifiable concentrates were prepared by the method set forth in Preparation Example 2 hereof of Compounds (1) and (2) of this invention and the racemate, and diluted 2000 times with water. Each diluted liquid was sprayed onto Chinese cabbage fields in the following methods, and 1 week after the spraying the whole plants were pulled up and the numbers of surviving insects and the degree of phytotoxicity to the plants were noted.

Division of Areas: each area 5 m², 3 replications

Quantity Sprayed: 100 l/10 are

Vegetable: Chinese Cabbage (Variety: Nigo), 5-6 leaf stage.

TABLE 5

| Test Compound | Diluent Ratio | Common Cabbage Worms[1] | Diamond-back Moths[1] | Phyto-toxicity |
|---|---|---|---|---|
| 20% EC[3] of (1) | × 2000 | 0 | 1 | — |
| 20% EC[3] of (2) | × 2000 | 0 | 0 | — |
| 20% EC[3] of Racemate | × 2000 | 3 | 6 | +[2] |
| 45% WP[4] of Lannate[5] | × 2000 | 5 | 56 | — |
| Not Sprayed | — | 29 | 148 | — |

[1]Total insects for 3 areas
[2]Chlorosis was observed partially on new shoot portions.
[3]Abbreviation of 20% emulsifiable concentrate
[4]Abbreviation of 45% wettable powder
[5]general name: methomyl, chemical name: S—methyl-N—[(methylcarbamoyl)oxy]-thioacetimidate

EXAMPLE 6

Phytotoxicity to Fruit Trees

20% emulsifiable concentrates prepared as in Preparation Example 2 hereof of Compounds (1) and (2) of this invention and the racemate were sprayed on the new shoot of adult fruit trees by a hand-sprayer. The method of spraying was summarized in the following table.

| Species of Fruit Tree | Variety | Spraying Date | Observation Date | Plot area and Replication |
|---|---|---|---|---|
| Pear (*Pyrus serotina*) | Chojuro | April 15th | April 22nd | one main branch 5 replications |
| Citrus | Wase-unshu | May 7th | May 16th | one main branch 5 replications |

All the leaves sprayed were observed; leaf injury was separated to 6 grades, and the degree of phytotoxicity was calculated by the following equation.

Degree of phytotoxicity =

$$\frac{\Sigma \text{ (leaf injury index} \times \text{ number of the leaves belonging to the injury index)}}{5 \times \text{ total number of leaves observed}} \times 100$$

leaf injury index
 0: No injury
 1: Trace of leaf injury
 2: 10–30% of the leaf area was injured
 3: 30–60% of the leaf area was injured
 4: 60–80% of the leaf area was injured
 5: 80–100% of the leaf area was injured The phytotoxicity which was observed in this experiment was only chlorosis and the leaf injury index was divided by the area of chlorosis. The results obtained are shown in Table 6 below.

TABLE 2

| Test Compound | Conc. (ppm) | Degree of Phytotoxicity Pear | Degree of Phytotoxicity Citrus |
|---|---|---|---|
| (1) | 400 | 0.9 | 5.6 |
|  | 200 | 0.2 | 4.2 |
|  | 100 | 0.0 | 0.0 |
|  | 50 | 0.0 | 0.0 |
| (2) | 400 | 0.5 | 1.0 |
|  | 200 | 0.0 | 0.0 |
|  | 100 | 0.0 | 0.0 |
|  | 50 | 0.0 | 0.0 |
| Racemate | 400 | 17.0 | 37.4 |
|  | 200 | 6.8 | 29.8 |
|  | 100 | 5.1 | 5.9 |
|  | 50 | 0.5 | 4.1 |
| Untreated | — | 0.0 | 0.0 |

Insecticidal compositions containing as an active ingredient the esters of this invention are extremely useful, not only for general household use against such house pests as flies, mosquitoes, and cockroaches, but also in the protection of grain stores against harmful insects, such as grain mites, Indian meal moths (*Plodia interpunctella*), and rice weevils(*Sitopluilus zeamais*), and for protection against and eradication of insects which are harmful in agriculture and forestry, in particular the green rice leaf-hopper (*Nephotettix cincticeps*), smaller brown plant hopper (*Laodelphax striatellus*), rice stem borers (*Chilo suppressalis*), camphor silk moth (*Dictyoploca japonica*), common cabbage worms (*Pieris rapae*), army worms, diamondback moth (*Plutella xylostella*), cut worms and aphids.

By methods well known to those skilled in the art using as diluent assistant solvents which are generally employed for insecticides, the insecticides of this invention may be supplied as emulsifiable concentrates, powders, oils, aerosols, wettable powders, granules, fine granules, mosquito coils and other heated or non-heated fumigants and powders or solid preparations in which attractants inviting insects such as feeds have been incorporated, or like preparations. In general, the active ingredient can be present at a concentration of between about 0.1 and 90% by weight of the total composition.

The esters of this invention may be used alone, or their insecticidal activity may be increased by the addition of synergists such as α-[2-(2-butoxyethoxy)ethoxy]-4,5-methylenedioxy-2-propyltoluene (hereinafter termed piperonyl butoxide), which is a synergist for pyrethroids, 1,2-methylenedioxy-4-[2-(octylsulfinyl)-propyl] benzene (hereinafter termed sulfoxide), 4-(3,4-methylenedioxyphenyl)-5-methyl-1,3-dioxane (hereinafter termed safroxane), N-(2-ethylhexyl)-bicyclo(2,2,1-)hepta-5-ene-2,3-dicarboxyimide (hereinafter termed MGK-264), octachlorodipropyl ether (hereinafter termed S-421), IBTA (isobornyl thiocyano acetate), Leathane, Sesamex, or others.

An even more effective and stable insecticide constituent can be obtained by the addition of suitable quantities of stabilizers such as phenol derivatives, e.g., BHT, bis-phenol derivatives; or arylamines e.g., phenyl-α-naphthylamine, phenyl-α-naphthylamine and a condensate of phenetidine and acetone and the like.

Compositions with multiple objectives which may be expected to have a cooperative effect may be obtained by an admixture of other active constituents, for example, pyrethrin (extract of pyrethrum flowers) or allethrin, tetramethrin, dimethylmaleimide methyl chrysanthemate, 5-benzyl-3-furylmethyl chrysanthemate, 2-methyl-5-propargyl-3-furylmethylchrysanthemate, 5-propargylfurfuryl chrysanthemate and their optically active forms, or 3-phenoxybenzyl-2',2',3', 3'-tetramethylcyclopropane-1'-carboxylate, dimethylmaleimide methyl-2,2,3,3-tetramethylcyclopropane-1-carboxylate, 3-phenoxybenzyl chrysanthemate or other known pyrethroid insecticides, 1-naphthyl-N-methylcarbamate, 3,4-dimethylphenyl-N-methylcarbamate or other carbamate insecticides, DDT, BHC, Methoxychlor or other organic chlorine insecticides, O,O-dimethyl-O-(3-methyl-4-nitrophenyl)-phosphorothioate [hereinafter termed Sumithion (trademark registered by Sumitomo Chemical Co., Ltd.)], O,O-dimethyl-O-4-cyano-phenylphosphorothioate [Cyanox (trademark registered by Sumitomo Chemical Co., Ltd.)], DDVP, dimethoate or other organic phosphorus insecticides, chlordimeform (N'-(2-methyl-4-chlorophenyl)-N,N-dimethylformamidine), cartap (1,3-bis-(carbamoylthio)-2-(N,N-dimethylamino)-propane hydrochloride) or other insecticides or fungicides, nematicides, acaricides, herbicides, plant growth regulating agents, fertilizers, BT agent or other microbiological agricultural chemicals, insect hormones and the like agricultural chemicals, with the components of this invention.

The preparation and effectiveness of the insecticides of this invention will now be explained with reference to the following Preparation Examples and Test Examples; the invention is, of course, not to be construed as being limited by these examples. Unless otherwise indicated, all parts, ratios and the like are by weight.

PREPARATION EXAMPLE 1

0.1 part of each of Compounds (1) and (2) of this invention was dissolved in deodorized kerosene to obtain 100 parts of the respective oil preparations.

PREPARATION EXAMPLE 2

To 20 parts of each of Compounds (1) and (2) of this invention were added 70 parts of xylene and 10 parts of Sorpol 3005 (registered trademark of Toho Chemicals) and the mixture was dissolved by stirring well to obtain respective emulsifiable concentrates of the compounds.

PREPARATION EXAMPLE 3

To 5 parts of each of Compounds (1) and (2) of this invention were added 15 parts of safroxane, 10 parts of Sorpol SM-200 (registered trademark of Toho Chemicals) and 70 parts of xylol and the mixture was dissolved by stirring well to obtain respective emulsifiable concentrates of the compounds.

PREPARATION EXAMPLE 4

0.2 part of Compound (1) of this invention was dissolved by mixing with 0.1 part of (+) trans-chrysanthemate of (+) allethrolon, 7 parts of xylol and 7.7 parts of deodorized kerosene, and introduced into an aerosol container, which was then fitted with a valve. 85 parts of a propellant (liquified petroleum gas) was then introduced through this valve under pressure to obtain an aerosol preparation.

PREPARATION EXAMPLE 5

0.2 part of Compound (2) of this invention, 0.1 part of tetramethrin, 1.5 parts of piperonyl butoxide, 13.2 parts of deodorized kerosene and 1 part of Atomos 300 (registered trademark of the Atlas Chemical Company) as an emulsifier were mixed, emulsified with the addition of 49 parts of distilled water, and then introduced into an aerosol container together with 35 parts of a 3:1 mixture of deodorized butane and deodorized propane, to obtain a water-based aerosol preparation.

PREPARATION EXAMPLE 6

0.2 part of Compound (1) of this invention was dissolved by mixing with 0.2 part of tetramethrin, 0.2 part of Sumithion (trademark, as described above), 7.4 parts of xylol and 7 parts of deodorized kerosene, and an aerosol preparation was prepared in the same method as described in Preparation Example 4.

PREPARATION EXAMPLE 7

0.6 g of each of Compounds (1) and (2) of this invention was respectively dissolved in methanol and mixed uniformly by stirring with 99.4 g of a carrier (tabu powder:pyrethrum marc:powdered wood mixed in a ratio of 3:5:1). The methanol was evaporated off, and 150 ml of water added thereto. After sufficient kneading, each of the resulting preparation was moulded and dried to obtain a mosquito coil.

PREPARATION EXAMPLE 8

To 0.05 g of each of Compounds (1) and (2) of this invention was added 0.5 g respectively of 5-propargylfurfuryl chrysanthemate, and the resulting mixture was dissolved in an appropriate quantity of chloroform and then stuck onto asbestos having a size of 2.5 cm × 1.55 cm and a thickness of 0.3 cm to obtain a fumigant insecticide composition.

For a fiber carrier, a pulp plate or the like can be used instead of asbestos with the same effect.

PREPARATION EXAMPLE 9

1 part each of Compounds (1) and (2) of this invention was dissolved in 20 parts respectively of acetone, and after addition of 99 parts of 300 mesh talc, the resulting mixture was blended in a grinder while thoroughly stirring. The acetone was then evaporated off to obtain a respective powder preparation.

PREPARATION EXAMPLE 10

2 parts of 3,4-xylyl-N-methylcarbamate was added to 0.5 part of Compound (2) of this invention and the mixture was dissolved in 20 parts of acetone. A powder preparation was then obtained with the addition of 97.5 parts of 300 mesh talc in the same manner as in Preparation Example 9.

PREPARATION EXAMPLE 11

5 parts of Sorpol SM-200 (trademark as described above) was mixed well with 20 parts of Compound (1) of this invention and then mixed while thoroughly stirring in a grinder with 75 parts of 300 mesh diatomaceous earth to obtain a wettable powder.

PREPARATION EXAMPLE 12

5 parts of Toyo Lignin CT (registered trademark of Toyo Boseki) was added to 5 parts of Compound (1) of this invention and mixed while thoroughly stirring in a grinder with 90 parts of GSM clay (registered trademark of Jeeklite Mineral Industries). Next water was added thereto to the extent of 10% of the mixture, and after further stirring and mixing granules were made in a pelletizer, being afterwards dried in a stream of air.

PREPARATION EXAMPLE 13

90 parts of GSM clay (registered trademark of Jeeklite Mineral Industries) was added to 2 parts of Compound (1) of this invention, 3 parts of 1-naphthyl-N-methylcarbamate, and 5 parts of Toyo Lignin CT (registered trademark of Toyo Boseki), and mixed in a grinder with sufficient stirring. Next water was added to this mixture to the extent of 10% of the mixture, and after further stirring and mixing granules were produced using a pelletizer, being afterwards dried in a stream of air.

PREPARATION EXAMPLE 14

2 parts of 3,4-dimethylphenyl-N-methylcarbamate was added to in each case 3 parts of Compounds (1) and (2) of this invention and dissolved in a suitable quantity of acetone. Respective poisoned baits were prepared by adsorbing the solutions on 95 parts of solid mouse food. Apart from mouse food, sugar, starch, rice bran, powdered grain, yeast or the like may be used as carriers for the poisoned bait, and attractants to attract harmful insects may also be added with the object of eradicating them.

The effectiveness of the insecticides according to the invention which are obtained from the above described preparations is as follows.

TEST EXAMPLE 1

Spraying was carried out using a group of about 100 adult *Musca domestica* by the Campbell's turn-table method [*Soap and Sanitary Chemicals,* Vol. 14, No. 6, p. 119 (1938)] with 5 ml of the oil preparation obtained in Preparation Example 1, the spray being allowed to fall for 10 minutes. A mortality of 100% was obtained on the day following the exposure.

TEST EXAMPLE 2

10 l of water was placed in a polyethylene bucket of a capacity of 14 l, and 1 g of the granules prepared in the Preparation Example 12 was thrown in. After 1 day, about 100 last instar larvae of *Culex pipiens pallens* were released in the water, and the number surviving noted. After 24 hours, more than 90% of the larvae were killed.

TEST EXAMPLE 3

The effectiveness on adult *Musca domestica* of the aerosol preparations obtained in Preparation Examples 4, 5 and 6 was tested by the aerosol testing method [set out in *Soap and Chemical Specialities Blue Book* (1965)] using a Peat Grady chamber (a six feet cube).

With either aerosol 80% or more of the flies were knocked down within 15 minutes after spraying.

TEST EXAMPLE 4

Rice grown for 45 days after sowing in Wagner pots of a scale of one in 50,000 was dusted with the powder preparations obtained in Preparation Examples 9 and 10, in a proportion of 2 kg/10 are, using a bell-jar duster.

These were then covered with a wire mesh and 30 specimens of adult *Nephotettix cincticeps* released therein. After 1 day, 100% of the Nephotettix were killed.

TEST EXAMPLE 5

Chinese cabbage was cultivated in a vinyl resin house and army worms, common cabbage worms and diamondback moths were artificially parasitized thereon. The vinyl resin house (height 2 m) was then partitioned at intervals of 30 m², and fumigated by introducing 10 g of the wettable powders obtained in Preparation Example 11 into a fumigator (search). No spreading of the damage caused by harmful insects was observed thereafter.

While the invention has been described in detail and with reference to specific embodiments thereof, it will be apparent to one skilled in the art that various changes and modifications can be made therein without departing from the spirit and scope thereof.

What is claimed is:

1. An insecticidal composition consisting essentially of, as an active ingredient, an insecticidally effective amount of α-cyano-3-phenoxybenzyl S-(+)-2-(4-chlorophenyl)isovalerate or S-(−)-α-cyano-3-phenoxybenzyl S-(+)-2-(4-chlorophenyl)isovalerate and an inert carrier.

2. The insecticidal composition according to claim 1, wherein said active ingredient is α-cyano-3-phenoxybenzyl S-(+)-2-(4-chlorophenyl)isovalerate.

3. The insecticidal composition according to claim 1, wherein said active ingredient is S-(−)-α-cyano-3-phenoxybenzyl S-(+)-2-(4-chlorophenyl)isovalerate.

4. The insecticidal composition according to claim 1, wherein said active ingredient is present at a concentration of 0.1 to 90% by weight based on the total weight of said insecticidal composition.

5. An insecticidal composition comprising, as an active ingredient, an insecticidally effective amount of an optically active α-cyano-3-phenoxybenzyl S-(+)-2-(4-chlorophenyl)isovalerate substantially free of the other optical isomers of said compound and an inert carrier.

6. The insecticidal composition according to claim 5 wherein said active ingredient is S-(−)-α-cyano-3-phenoxybenzyl S-(+)-2-(4-chlorophenyl)isovalerate substantially free of R-(+)-α-cyano-3-phenoxybenzyl S-(+)-2-(4-chlorophenyl)isovalerate.

7. An insecticidal composition consisting of, as an active ingredient, α-cyano-3-phenoxybenzyl S(+)-2-(4-chlorophenyl)isovalerate or S-(−)-α-cyano-3-phenoxybenzyl S-(+)-2-(4-chlorophenyl)isovalerate, said isomers having substantially no phytotoxicity at practical application levels.

8. The isomer α-cyano-3-phenoxybenzyl S-(+)-2-(4-chlorophenyl)isovalerate substantially free of the other optical isomers of said isomer.

9. The isomer S-(−)-α-cyano-3-phenoxybenzyl S-(+)-(4-chlorophenyl)isovalerate substantially free of the other optical isomers of said isomer.

10. The optical isomer S-(−)-α-cyano-3-phenoxybenzyl S-(+)-α-isopropyl-p-chlorophenylacetate.

11. α-Cyano-3-phenoxybenzyl S-(+)-2-(4-chlorophenyl)isovalerate.

12. S-(−)-α-Cyano-3-phenoxybenzyl S-(+)-2-(4-chlorophenyl)isovalerate.

13. A method for killing insects, which comprises applying the insecticidal composition according to claim 1 in such a manner that the active ingredient contacts said insects in an insecticidally effective amount.

* * * * *